(12) United States Patent
Wei et al.

(10) Patent No.: US 8,430,103 B2
(45) Date of Patent: Apr. 30, 2013

(54) FIXING/RELEASING MECHANISM AND THE BASE USING SUCH MECHANISM

(75) Inventors: Bo Wei, Wuxi (CN); Yalan Yang, Wuxi (CN); Lanping Liu, Wuxi (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 1328 days.

(21) Appl. No.: 12/171,203

(22) Filed: Jul. 10, 2008

(65) Prior Publication Data

US 2009/0013731 A1 Jan. 15, 2009

(30) Foreign Application Priority Data

Jul. 13, 2007 (CN) .......................... 2007 1 0129172

(51) Int. Cl.
*A61B 19/00* (2006.01)
*F16B 21/08* (2006.01)
*A44B 17/00* (2006.01)

(52) U.S. Cl.
USPC ........... 128/897; 403/321; 403/325; 403/327; 24/369

(58) Field of Classification Search ............... 128/897; 403/321, 325–327; 24/369; 254/104
See application file for complete search history.

(56) References Cited

U.S. PATENT DOCUMENTS

| | | | |
|---|---|---|---|
| 4,096,856 A | 6/1978 | Smith et al. | |
| 4,227,762 A | 10/1980 | Scheiner | |
| 4,454,382 A | 6/1984 | Borne et al. | |
| 5,248,264 A | 9/1993 | Long et al. | |
| 5,375,604 A | 12/1994 | Kelly et al. | |
| 5,488,537 A | 1/1996 | Heald et al. | |
| 5,622,179 A * | 4/1997 | Pfandal et al. | 128/897 |
| 5,921,697 A | 7/1999 | Karl et al. | |
| 5,946,186 A | 8/1999 | Karl et al. | |
| 6,138,968 A | 10/2000 | Svantesson et al. | |
| D470,849 S | 2/2003 | Bertagnole et al. | |
| 6,865,418 B2 | 3/2005 | Merry | |
| D566,118 S | 4/2008 | Brassard | |
| 7,633,750 B2 * | 12/2009 | Fan et al. | 361/679.43 |
| 2003/0167074 A1 | 9/2003 | Merry | |
| 2004/0075980 A1 * | 4/2004 | Park | 361/686 |

* cited by examiner

*Primary Examiner* — Charles A Marmor, II
*Assistant Examiner* — Thaddeus Cox
(74) *Attorney, Agent, or Firm* — Armstrong Teasdale LLP

(57) ABSTRACT

The present invention provides a base for placement of a medical apparatus, comprising: a base body provided with a platform for carrying said medical apparatus, and a fixing/releasing mechanism for fixing and releasing said medical apparatus, the fixing/releasing mechanism comprising a lock hook for fixing/releasing the medical apparatus; the fixing/releasing mechanism further comprising: a press-fit button including an operation key exposed above the base body; the operation key is protrudably and retractably received in a key through hole in the base body, the operation key moving in the direction of the force when being subjected to a pressure to be received in the key through hole; when the applied force disappears, the operation key automatically returns to the original position and protrudes out of the key through hole; a snap catch mechanism comprising said lock hook protrudably and retractably received in a lock hook receiving portion in the base body; a transmission mechanism connected to said press-fit button and transmitting the pressure applied to the press-fit button to said snap catch mechanism so that the lock hook of the snap catch mechanism generates a protrudable and retractable movement and protrudes out of the lock hook receiving portion to lock said medical apparatus or retract in the lock hook receiving portion and release said medical apparatus.

20 Claims, 8 Drawing Sheets

FIXING/RELEASING MECHANISM AND THE BASE USING SUCH MECHANISM

CROSS REFERENCE TO RELATED APPLICATIONS

This application claims the benefit of Chinese Patent Application No. 200710129172.9 filed Jul. 13, 2007, which is hereby incorporated by reference in its entirety.

FIELD OF THE INVENTION

The subject matter disclosed herein relates to fixing/releasing mechanisms, particularly to a structure fixing an apparatus such as a portable or hand-held medical equipment to a base.

BACKGROUND OF THE INVENTION

A fixing/releasing mechanism is used to mechanically connect an element to another element. The current apparatuses such as medical apparatuses increasingly tend to be portable and detachable to meet the portablility and use requirement in various environments. For example, the U.S. patent application US2003/0167074A1 published on Sep. 4, 2003, as shown in FIG. 1, reveals that an extended base of a cart has a fixing/releasing mechanism to couple and snap fit a portable medical apparatus placed on the extended base. However, the fixing/releasing mechanism fixes the medical apparatus to the base only by means of front and rear clamps 40, 78, 80 etc. and requires manual operation for fixing and positioning so that the fixing and mounting process is inconvenient and when the portable medical apparatus is removed, it is likely to be damaged by impingement of impact force in opposite direction generated by the clamps 40, 78, 80 when breaking away from the medical apparatus.

BRIEF DESCRIPTION OF THE INVENTION

In one aspect, a fixing/releasing mechanism for solving the above problem and a base and a medical apparatus using said fixing/releasing mechanism are provided, exhibiting a better convenience for operation.

In another aspect, a fixing/releasing mechanism for solving the above problem and a base and a medical apparatus using said fixing/releasing mechanism are provided, exhibiting a relatively stable snap fitting mounting process.

In one embodiment, a fixing/releasing mechanism is used to connect two units and is mounted on one of said two units, the fixing/releasing mechanism comprising: a press-fit button which, when under a pressure, moves in a direction of the force and automatically returns to the original position when the applied force disappears; a snap catch mechanism comprising a lock hook for fixing one unit to the other or releasing one unit from the other; a transmission mechanism connected to said press-fit button and transmitting the pressure applied to the press-fit button to said snap catch mechanism so that the lock hook of the snap catch mechanism generates protrudable and retractable movement so as to fix one unit to the other or releasing the other unit from said one unit.

Said snap catch mechanism further comprises a liftable bracket, the liftable bracket including a lock hook base and said lock hook, said lock hook extending upwardly from the lock hook base, a contact surface being disposed on said lock hook base in a direction opposite to the extension direction of said lock hook; said transmission mechanism comprising a lock hook liftable portion; said lock hook liftable portion is a latch and comprises a push surface, the push surface being able to contact with the contact surface on the lock hook base and moveable forward and backward relative to the contact surface of the lock hook base so as to bring the protrudable and retractable movement of the lock hook base and said lock hook.

At least one of the front ends of the push surface of said lock hook liftable portion and the contact surface of the lock hook base is provided with a wedge-shaped structure which is a ramp inclined downwardly.

Each of the front ends of the push surface of said lock hook liftable portion and the contact surface of the lock hook base is provided with a downwardly inclined ramp, the contact surface of the lock hook base further comprising a bottom plane extending out from the bottom of its ramp, the push surface of said lock hook liftable portion having an upper plane extending from the upper portion of the ramp.

Said snap catch mechanism further comprises a lock hook buffer and a lock hook elastomer; upon mounting, said lock hook buffer is fixed on the unit where the fixing/releasing mechanism is mounted; said lock hook buffer having a top portion being increasingly rising multiple planes and exposed on the front surface of the mounted unit to buffer the impact generated when the lock hook of the snap catch mechanism releases the other unit; said locking hook elastomer is disposed between a lower surface of the top portion of the locking hook buffer and the locking hook base of the liftable bracket so that the locking hook elastomer abuts against a surface of the locking hook base on one side of the extension direction of the locking hook.

A plurality of positioning posts extend out from a lower surface of the top portion of the lock hook buffer; said locking hook base is provided with a plurality of through holes matching said plurality of positioning posts; said lock hook elastomer is a plurality of springs sleeved onto the positioning posts.

Said press-fit button comprises an operation key and a button elastomer, said transmission mechanism comprises a fixed panel located at the other end opposite to one end of the push surface of the lock hook liftable portion, said button elastomer brings, driven by the push force transmitted from the operation key, the fixed panel to move and pushes the push surface of the transmission mechanism to move along the contact surface of the snap catch mechanism; said button elastomer is a spring whose both ends are respectively connected to the operation key of the press-fit button and the fixed panel of the transmission mechanism.

Said press-fit button further comprises a button bracket that is, upon mounting, fixed to the mounting unit; said operation key is fixed to the fixed panel of the transmission mechanism and the button elastomer abuts against between the fixed panel of the transmission mechanism and the button bracket.

Said transmission mechanism further comprises a pull lever and a diverting transmission means; one end of said pull lever comprises sad fixed panel fixedly connected to the operation key, the other end is connected to one end of the diverting transmission means, the other end of the diverting transmission means is connected to the other end of the lock hook liftable portion opposite to one end of the push surface; the diverting transmission means is connected between the pull lever and both ends of the lock hook liftable portion to transmit the movement of the pull lever to the lock hook liftable portion and converts forward or backward movement of the pull lever into backward or forward movement of the lock hook liftable portion.

Said diverting transmission means is a diverting linkage rotatably connected between the pull lever and both ends of the lock hook liftable portion and allows the pull lever and the lock hook liftable portion not to be on the same straight line; upon mounting, at any position between both ends of the diverting linkage is provided a supporting rotation shaft point by virtue of which the diverting linkage can be rotatably fixed to the mounting unit.

Said diverting transmission means is a gear.

Each of the pull lever and the lock hook liftable portion is provided with a slide slot so as to be slidingly fixed to the mounting unit upon mounting.

Said button bracket comprises a supporting planar body supporting and abutting against the button elastomer, an upper and a lower fixed planar bodies extending along both ends of the supporting planar body towards each other; an elastic support shaft is provided on the supporting plane to support the button elastomer and position movement of the button elastomer and the operation key said upper and lower fixed planar bodies are fixed to the mounting unit upon mounting.

In another embodiment, a base for placement of a medical apparatus includes a base body provided with a platform for carrying said medical apparatus, and a fixing/releasing mechanism for fixing and releasing said medical apparatus, the fixing/releasing mechanism comprising a lock hook for fixing/releasing the medical apparatus; the fixing/releasing mechanism further comprising: a press-fit button including an operation key exposed above the base body; the operation key is protrudably and retractably received in a key through hole in the base body, the operation key moving in the direction of the force when being subjected to a pressure to be received in the key through hole; when the applied force disappears, the operation key automatically returns to the original position and protrudes out of the key through hole; a snap catch mechanism comprising said lock hook protrudably and retractably received in a lock hook receiving portion in the base body; a transmission mechanism connected to said press-fit button and transmitting the pressure applied to the press-fit button to said snap catch mechanism so that the lock hook of the snap catch mechanism generates a protrudable and retractable movement and protrudes out of the lock hook receiving portion to lock said medical apparatus or retract in the lock hook receiving portion and release said medical apparatus.

Said snap catch mechanism further comprises a liftable bracket, the liftable bracket including a lock hook base and said lock hook, said lock hook extending upwardly from the lock hook base, a contact surface being disposed on said lock hook base in a direction opposite to the extension direction of said lock hook; said transmission mechanism comprising a lock hook liftable portion; said lock hook liftable portion is a latch and comprises a push surface, the push surface being in contact with the contact surface on the lock hook base and moveable forward and backward relative to the contact surface of the lock hook base so as to bring the protrudable and retractable movement of the lock hook base and said lock hook.

At least one of the front ends of the push surface of said lock hook liftable portion and the contact surface of the lock hook base is provided with a wedge-shaped structure which is a ramp inclined downwardly.

Each of the front ends of the push surface of said lock hook liftable portion and the contact surface of the lock hook base is provided with a downwardly inclined ramp, the contact surface of the lock hook base further comprising a bottom plane extending out from the bottom of its ramp, the push surface of said lock hook liftable portion having an upper plane extending from the upper portion of the ramp.

Said snap catch mechanism further comprises a lock hook buffer and a lock hook elastomer; upon mounting, said lock hook buffer is fixed on a snap catch mechanism seat of the base body; said lock hook buffer having a top portion being increasingly rising multiple planes and exposed outside of the base body to buffer the impact generated when the lock hook of the snap catch mechanism releases the medical apparatus; said locking hook elastomer is disposed between a lower surface of the top portion of the locking hook buffer and the lock hook base of the liftable bracket so that the locking hook elastomer abuts against the lock hook base surface on one side of the extension direction of the lock hook.

A plurality of positioning posts extend out from a lower surface of the top portion of the lock hook buffer; said locking hook base is provided with a plurality of through holes matching said plurality of positioning posts; said lock hook elastomer is a plurality of springs sleeved onto the positioning posts; said lock hook buffer is fixed to the snap catch mechanism seat via the plurality of positioning posts in cooperation with screws.

Said press-fit button further comprises a button elastomer, said transmission mechanism comprises a fixed panel located at the other end opposite to one end of the push surface of the lock hook liftable portion, said button elastomer brings, driven by the push force transmitted from the operation key, the fixed panel to move and pushes the push surface of the transmission mechanism to move along the contact surface of the snap catch mechanism.

Said button elastomer is a spring whose both ends are respectively connected to the operation key of the press-fit button and the fixed panel of the transmission mechanism.

Said press-fit button further comprises a button bracket fixed to the base body; said operation key is fixed to the fixed panel of the transmission mechanism and the button elastomer abuts against between the fixed panel of the transmission mechanism and the button bracket.

Said transmission mechanism further comprises a pull lever and a diverting transmission means; one end of said pull lever comprises sad fixed panel fixedly connected to the operation key, the other end is connected to one end of the diverting transmission means, the other end of the diverting transmission means is connected to the other end of the lock hook liftable portion opposite to one end of the push surface; the diverting transmission means is connected between the pull lever and both ends of the lock hook liftable portion to transmit the movement of the pull lever to the lock hook liftable portion and converts forward or backward movement of the pull lever into backward or forward movement of the lock hook liftable portion.

Each of the pull lever and the lock hook liftable portion is provided with a slide slot so as to be slidingly fixed to the body of the base.

Said diverting transmission means is a diverting linkage rotatably connected between the pull lever and both ends of the lock hook liftable portion and allows the pull lever and the lock hook liftable portion not to be on the same straight line; at any position between both ends of the diverting linkage is provided a supporting rotation shaft point by virtue of which the diverting linkage can be rotatably fixed to the body of the base.

Said diverting transmission means is a gear.

Said button bracket comprises a supporting planar body supporting and abutting against the button elastomer, an upper and a lower fixed planar bodies extending along both ends of the supporting planar body towards each other; an elastic support shaft is provided on the supporting planar body to support the button elastomer and position movement of the button elastomer, the fixed panel of the transmission mechanism and the operation key; said upper and lower fixed planar bodies are fixed to the body of the base.

At the opposite two ends of the platform a front and a rear side stands extend upwardly from the base body; said lock hook receiving portion is provided on the platform adjacent to the front side stand; said transmission mechanism is provided on the lower portion of the base body.

On the platform of the base a side mounting guide rail extends from at least one of left and right sides adjacent to the rear side stand.

The side mounting guide rail comprises a first functional surface and a second functional surface extending out along the first functional surface, the first and second functional surfaces are ramps extending upwardly and outwardly along the inside of the side mounting guide rail from the platform so that the first functional surface is tangential to an end angle of the medical apparatus cooperating therewith; the second functional surface moves outwardly relative to the first functional surface and an angle is formed between the first functional surface and the second functional surface.

The fixing/releasing mechanism of the embodiments described herein facilitate automatically coupling one unit such as a medical apparatus to a unit such as a base on which the fixing/releasing mechanism is mounted via the press-fit button, the transmission mechanism and the snap catch mechanism. As such, the embodiments described herein do not need any manually operated button. The medical apparatus presses the press-fit button to push the button to move inwardly of the base to push the transmission mechanism to move forwardly and move along the contact surface of the lock hook base of the lock hook mechanism; the horizontal movement of the transmission mechanism is converted into up-and-down movement of the lock hook base via the push surface of the wedge-shaped structure of the transmission mechanism and the contact surface of the wedge-shaped structure of the lock hook base so as to bring the lock hook on the base to make protrudable and retractable movement in the lock hook receiving portion of the base. When the medical apparatus is removed, the push of the medical apparatus to the press-fit button is reduced or eliminated, so the press-fit button automatically returns to the original position driven by a return force of the elastomer to bring the transmission mechanism to move backward to eliminate the upward pushing force of the snap catch mechanism. Furthermore, the lock hook of the snap catch mechanism also, driven by the return force of its elastomer, automatically returns to its original position to be concealed in the lock hook receiving portion of the base so as to eradicate the possible damages caused by the lock hook to the medical apparatus.

Besides, according to the present invention a lock hook buffer is provided to be raised a certain height to prevent any collision to the medical apparatus after the medical apparatus breaks away from the lock hook and before the lock hook completely sinks.

Meanwhile, two side mounting guide rails are provided on both sides of the rear end of the base to improve the positioning degree and efficiency of the operating and mounting to avoid collision between the connector and the medical apparatus due to improper positioning. Besides, the two side mounting guide rails further comprise two upwardly and outwardly inclined ramps connected in stepped manner to buffer the impact caused by the press-fit button and the lock hook when the medical apparatus breaks away from the lock hook on the base so that the medical apparatus can be removed smoothly.

DETAILED DESCRIPTION OF THE INVENTION

Figure 1:
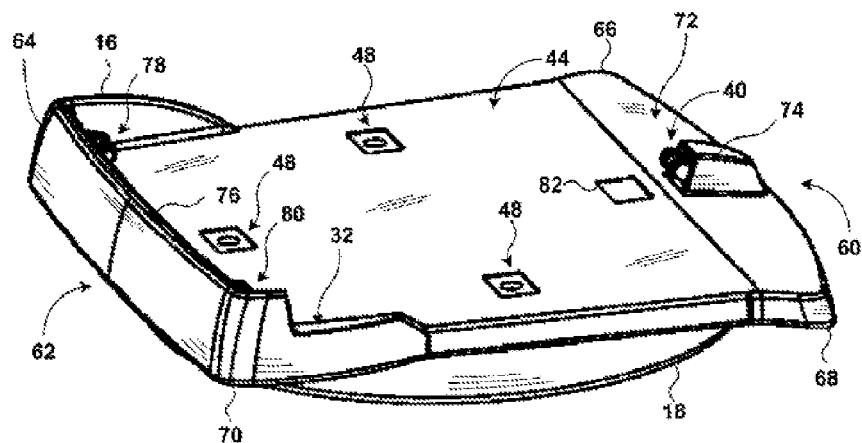
FIG. 1 is a view showing the structure of the base having a locking hook in the prior art.
Figure 2:
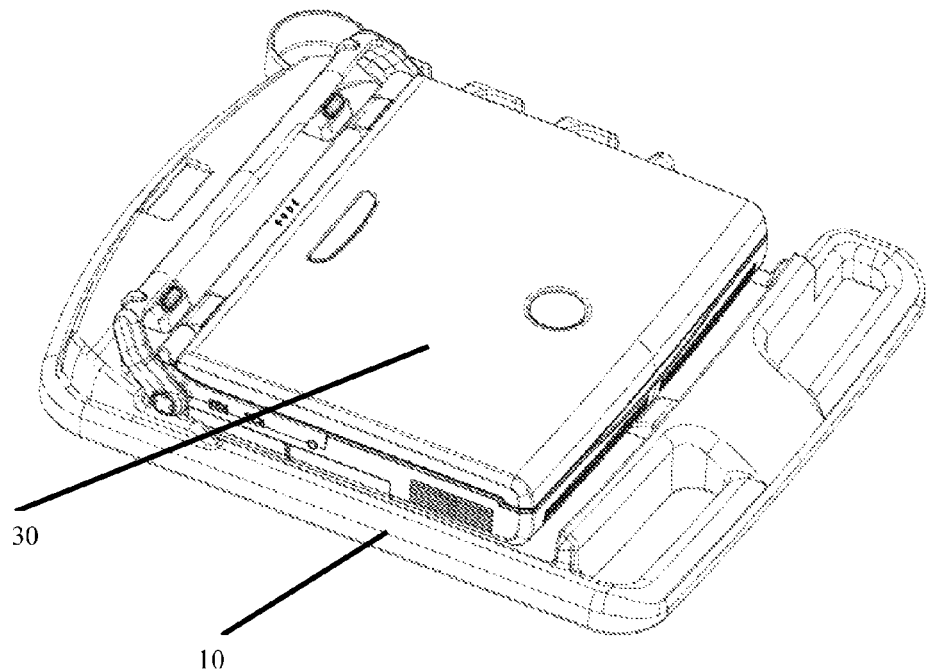
FIG. 2 is a view showing an exemplary base equipped with a medical apparatus.
Figure 3:
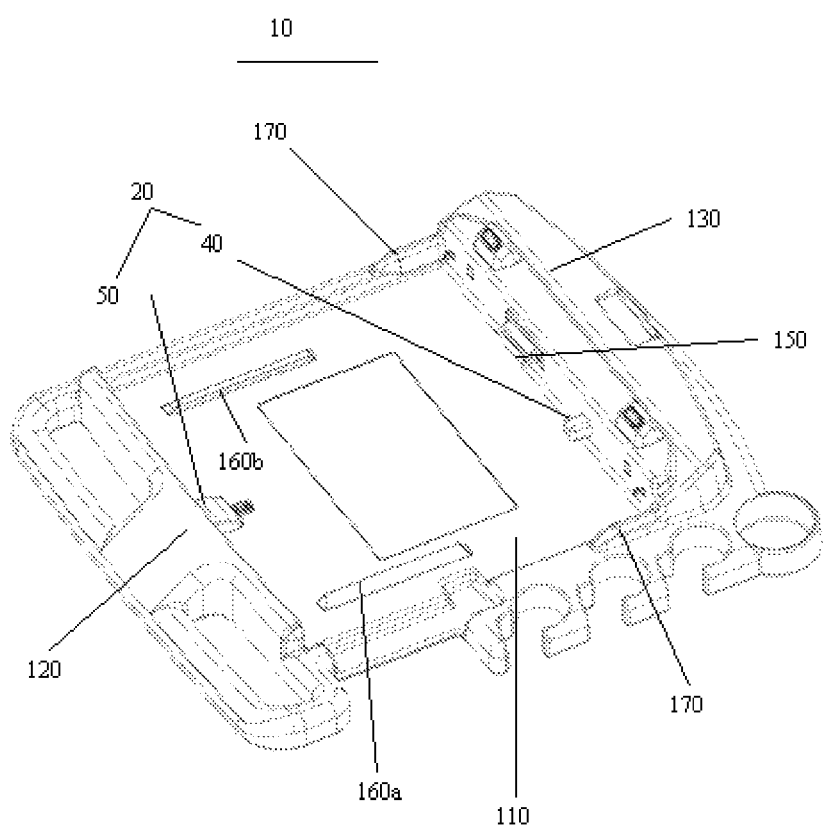
FIG. 3 and FIG. 9 are views showing the structure of the base of FIG. 2 as seen from the front side.

FIG. 2 is a view showing connection of two units 10, 30 via an exemplary fixing/releasing mechanism 20 (as shown in FIG. 3). The unit 30 is an ultrasonic diagnosis apparatus sized and shaped similar to a notebook PC (personal computer). Another unit 10 is for example a base for placement of the ultrasonic diagnosis apparatus, wherein the base has an electronic circuit, a power source circuit and other accessories for function extension of the ultrasonic diagnosis apparatus. The base is disposed on an ultrasonic diagnosis apparatus deck having wheels for moving such as a cart.

The unit 30 is not limited to the ultrasonic diagnosis apparatus, it can be a suitable electronic apparatus such as cardiac defibrillator or a monitor or non-electronic apparatuses. The unit 10 is not limited to a base of a cart for the ultrasonic diagnosis apparatus, and it can be a support base for use in the electronic or non-electronic apparatuses. In this case, it does not necessarily have moveable wheels.

In the embodiment, the unit 30 is an ultrasonic diagnosis apparatus and the unit 10 is a base on a cart for supporting the ultrasonic diagnosis apparatus 30. Certainly, in the event of combined devices in any other combination manners, the same functions and effects can be obtained.

The ultrasonic diagnosis apparatus 30 is engaged with the cart by means of the base 10 on the cart (not shown) to form a fully equipped ultrasonic diagnosis system. The ultrasonic diagnosis apparatus 30 can be moved away from the base 10 of the cart and can be used as an individual apparatus as a fundamental ultrasonic diagnosis meter and as a portable or a hand-held apparatus for convenient use.

FIG. 3 is a schematic view of the base 10. The base 10 comprises a base body on which a platform 110 is provided to carry said ultrasonic diagnosis apparatus 30. A front side stand 120 and a rear side stand 130 extend from the body at the opposite two ends of the platform 110 to prevent the ultrasonic diagnosis apparatus 30 from sliding off from the base 10.

Figure 4:
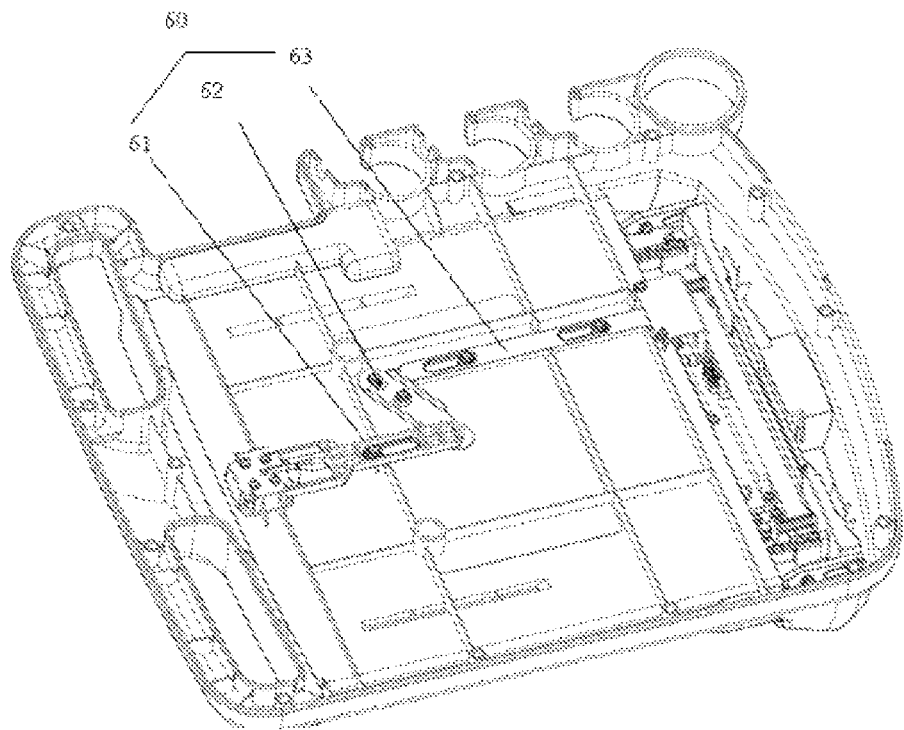
FIG. 4 and FIG. 10 are schematic views of an exemplary fixing/releasing mechanism in a non-force-applied state and a force-applied state.
Figure 5:
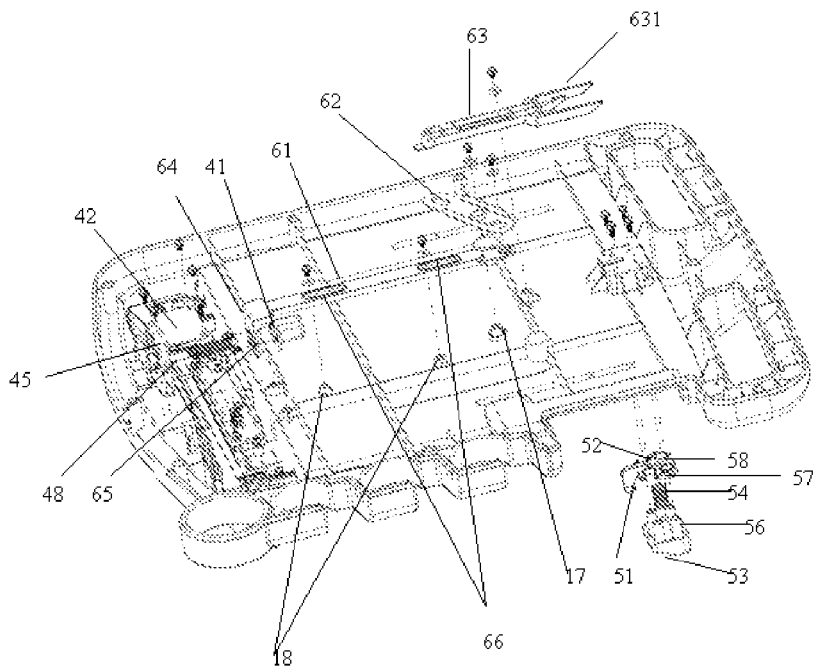
FIG. 5 and FIG. 6 are exploded views of the structure as seen from the bottom of the base shown in FIG. 2.

A fixing/releasing mechanism 20 is provided on the body of the base 10 and comprises a press-fit button 40 projecting from the inside of the rear side stand 130 and a snap catch mechanism 50 exposed on the platform 110 and a transmission mechanism 60 on the bottom of the body of the base 10 (as shown in FIGS. 4 and 5). The press-fit button 40, when under a pressure, moves in a direction of the force and automatically returns to the original position when the applied force disappears. The snap catch mechanism 50 is used to fix an apparatus such as the ultrasonic diagnosis apparatus to the base 10 or to release the apparatus from the base 10. The transmission mechanism 60 is connected to the press-fit button 40 and transmits the pressure applied to the press-fit button 40 to the snap catch mechanism 50 so that the snap catch mechanism 50 moves upwardly or downwardly such that the a locking hook 51 of the snap catch mechanism 50 rises to lock the ultrasonic diagnosis apparatus 30 or moves downwardly to release the ultrasonic diagnosis apparatus 30. As such, the ultrasonic diagnosis apparatus is fixed to the base 10 or released from the base 10.

Figure 6:
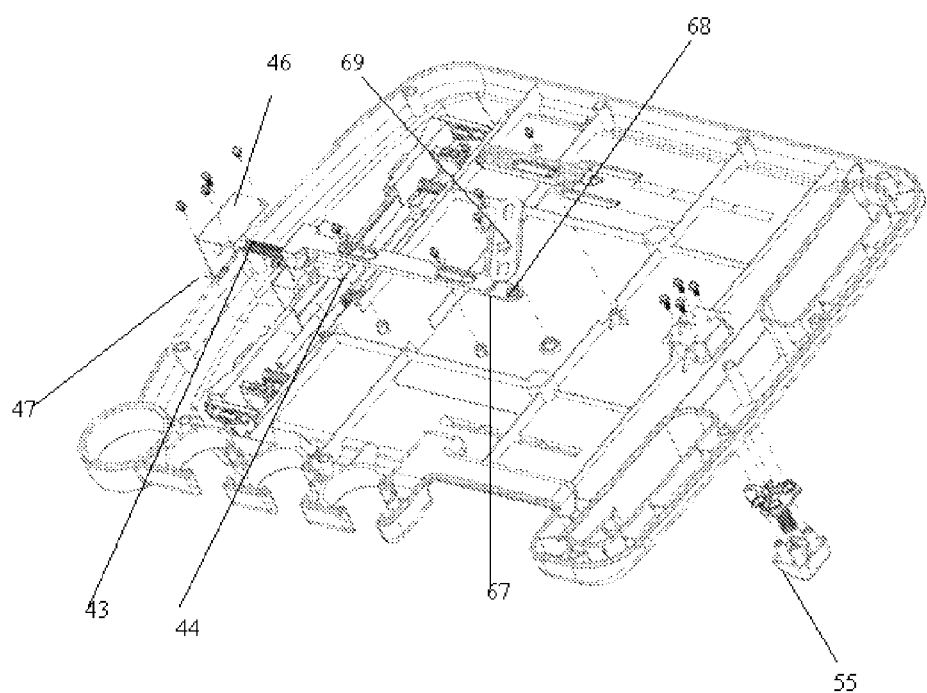
Figure 9:
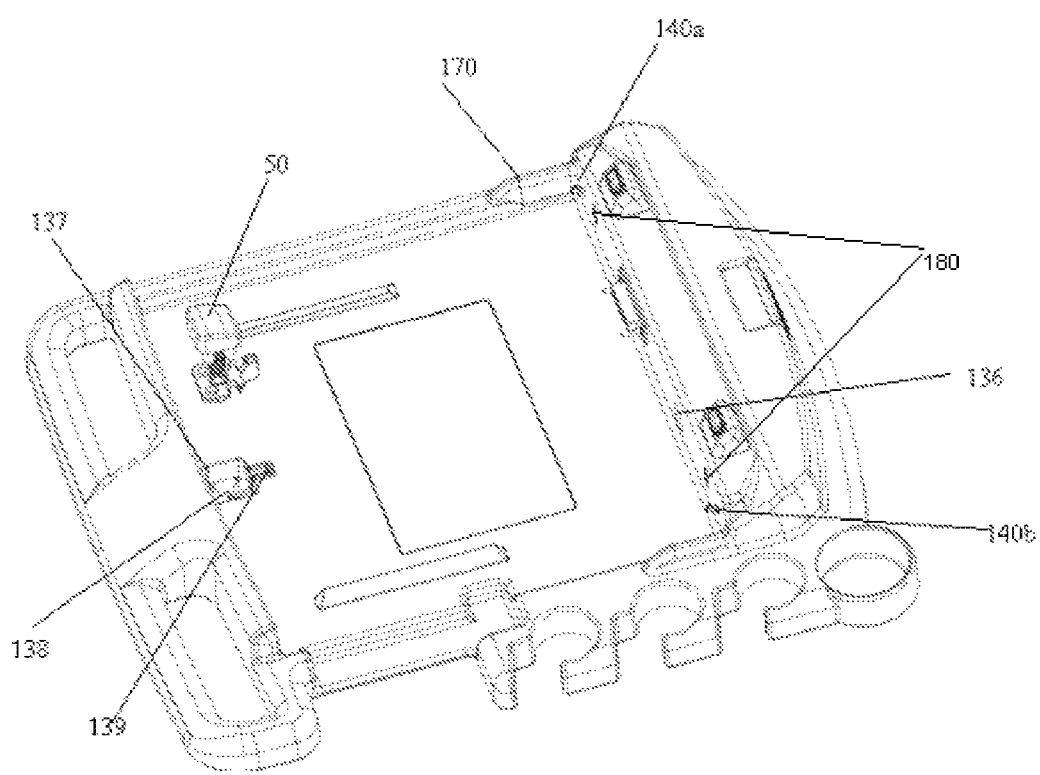

Meanwhile referring to FIGS. 4, 5 and 6, the figures show different states of the fixing/releasing mechanism 20 as seen from the bottom portion of the base 10. The press-fit button 40 comprises an operation key 41, a button bracket 42, and a button elastomer 43. The operation key 41 has a key top surface 44 for contacting with an external device and includes four walls extending from the key top surface 44 so as to constitute a semi-closed barrel body having an opening. The button bracket 42 includes a support planar body 45, an upper fixing planar body 46, and a lower fixing planar body 47 perpendicular to the support planar body 45 extending along the upper and lower ends of the support planar body 45 in opposite extension directions so as to form a fold-like step structure body. The upper and lower fixing planar bodies 46, 47 are respectively fixed to the upper and lower tables which are on the bottom of the body of the base 10 and have different heights, by means of screws in this embodiment. The support planar body 45 is provided with an elastic support shaft 48 to position the button elastomer 43. The button elastomer 43 can be a spring. Upon assembly, the button bracket 42 is fixed to a corresponding position of the bottom of the body of the base 10, the button elastomer 43 is sleeved onto the elastic support shaft 48 on the button bracket 42, then the operation key 41 is sleeved onto the elastic support shaft 48, and the operation key 41 projects from the bottom of the body of the base 10 above the body of the base 10 (as shown in FIG. 3) through a key through hole 136 (as shown in FIG. 9) of the base 10. When an external force is applied to the operation key 41, the operation key 41, under pressure of the external force, presses the button elastomer 43 to compress towards the support planar body 45 in the rear along the elastic support shaft 48, and moves backwards along with the button elastomer 43 so as to be hidden in the key through hole 136.

Figure 7:
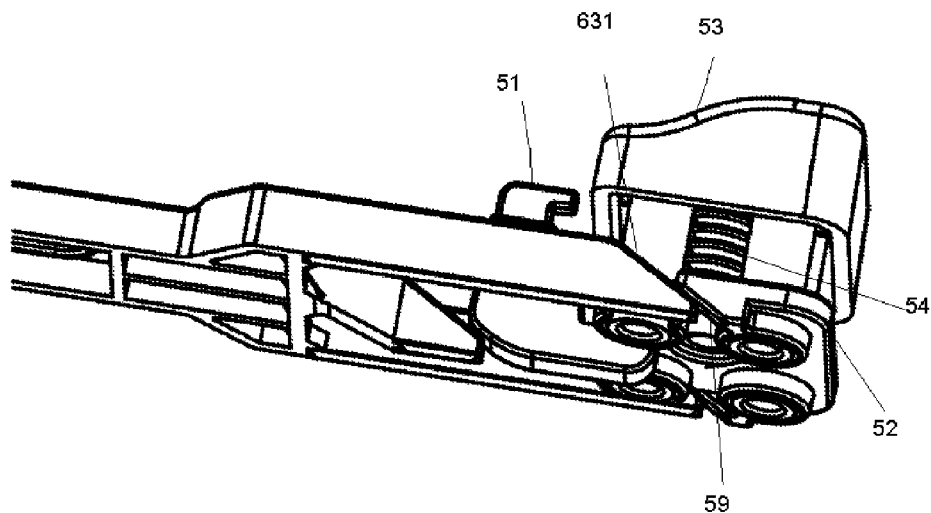
FIG. 7 and FIG. 8 are schematic views showing interaction between a transmission mechanism and a snap catch mechanism in the fixing/releasing mechanism shown in FIGS. 4 and 10.
Figure 8:
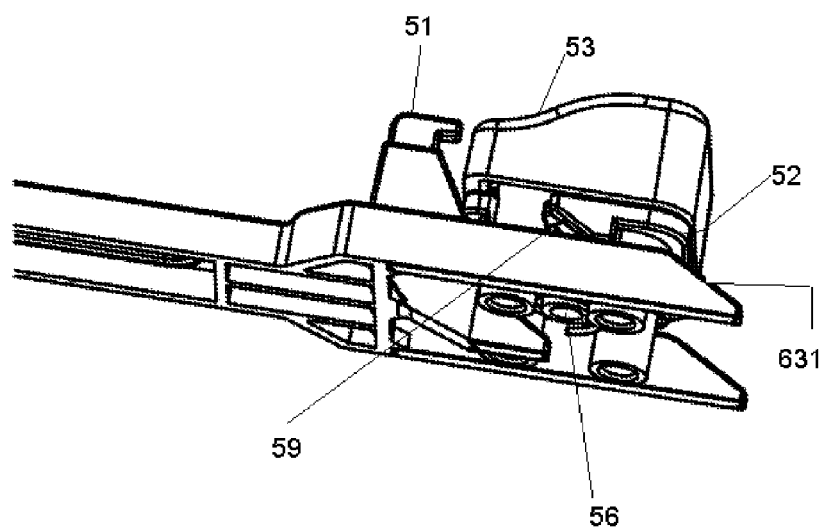

Meanwhile referring to FIG. 7 and FIG. 8, the snap catch mechanism 50 comprises a liftable bracket 52 having a locking hook 51, a locking hook buffer 53 and a locking hook elastomer 54. The locking hook buffer 53 comprises a buffer top portion 55 which outer surface is a ramp formed by a plurality of gradually rising planes to buffer impact generated when the locking hook 51 of the snap catch mechanism 50 releases the apparatus 30. The locking hook buffer 53 also includes one or more positioning posts 56 extend out from the lower surface of the buffer top portion 55 to position the locking hook elastomer 54 and the liftable bracket 52, and the locking hook buffer 53 is fixed to the body of the base 10 via the positioning posts 56. The liftable bracket 52 comprises a locking hook 51 and a locking hook base 57, wherein the locking hook 51 extends outwardly from the locking hook base 57. The locking hook base 57 has a through hole or opening 58 matching positioning posts 56 of the locking hook buffer 53. A contact surface 59 is provided on both sides of the locking hook base 57 to interact with the transmission mechanism 60. The contact surface 59 extends in a direction opposite to the direction in which the locking hook 51 extends. In this embodiment, the locking hook 51 extends upwardly, the contact surface 59 extends downward, and furthermore the contact surface 59 is a ramp downwardly inclined. The contact surface 59 further comprises a bottom plane extending outwardly from the bottom of the ramp. The locking hook elastomer 54 can be a spring. Upon assembly, the locking hook elastomer 54 is sleeved onto the positioning posts 56, the liftable bracket 52 is sleeved onto the positioning posts 56 having the locking hook elastomer 54 through a guide hole 58 on the locking hook base 57, so that the locking hook elastomer 54 is disposed between the lower surface of the top portion of the locking hook buffer 53 and the locking hook base 57, and the locking hook elastomer 54 abuts against a surface of the locking hook base 57 on one side of the extension direction of the locking hook 51 so that the liftable bracket 52 can move up and down along the positioning posts 56 upon applied with an upward thrust force.

Meanwhile referring to FIG. 9, in order to cooperate with and fix said snap catch mechanism 50, a snap catch mechanism seat 137 is provided on the platform 110 of the body of the base 10 adjacent to the front side stand 120. The snap catch mechanism seat 137 has a locking hook base receiving portion 138 for receiving the snap catch mechanism 50 and a locking hook receiving portion 139. The locking hook base receiving portion 138 is provided with positioning holes for example screw holes (not marked with a reference number) in the embodiment to fix the locking hook buffer 53 to the snap catch mechanism seat 137 on the body of the base 10 via fasteners such as screws in cooperation with the positioning posts on the locking hook buffer 53. The contact surface 59 on the locking hook base 57 projects out of the bottom of body of the base 10 via the locking hook base receiving portion 138 so as to cooperate with the transmission mechanism 60. The buffer top portion 55 of the locking hook buffer 53 is exposed to the upper surface of the body of the base 10. In a natural state and a non-force applied situation, the locking hook 51 is received and concealed in the locking hook receiving portion 139; when the transmission mechanism 60 interacts with the contact surface 59 to generate an upward thrust force thereto, the liftable bracket 52 urges the locking hook elastomer 54 to compress upwardly to move upwardly and urges the locking hook 51 to move upwardly to expose on the upper surface of the body of the base 10. When the external force applied to the contact surface 59 disappears, the locking hook elastomer 54 returns to the original position driven by its elastic return force and brings the liftable bracket 52 to move downwardly so that the locking hook 51 returns to the original position and conceals in the locking hook receiving portion 139.

Referring to FIG. 5 and FIG. 6 again, the transmission mechanism 60 comprises a pull lever 61, a diverting transmission means 62 and a locking hook lifting portion 63, wherein the turning transmission means 62 is connected between the pull lever 61 and both ends of the locking hook lifting portion 63 to transmit the movement of the pull lever 61 to the locking hook lifting portion 63 and convert a forward or backward movement of the pull lever 61 into a backward or forward movement of the locking hook lifting portion 63. A fixed panel 64 is provided at one end of the pull lever 61 and fixedly connected to the operation key 41, and the a through hole 65 is provided on the fixed panel 64 to allow the elastic support shaft 48 to freely pass. The fixed panel 64 is located between the operation key 41 and the button elastomer 43 and abuts against the button elastomer 43. When the button elastomer 43 is in a natural state, the operation key 41 is ensured to expose out of the front side stand 120 of the body of the base 10. To better position movement direction of the pull lever 61, one or more slide grooves 66 are provided on the body of the pull lever 61, a positioning post 18 is correspondingly provided on the bottom of the body of the base 10 to allow the slide groove 66 to move along the positioning post 18.

In this embodiment, said diverting transmission means 62 is a diverting linkage 62 whose one end is rotatably connected to another end 67 of the pull lever 61 opposite to the end having the fixed panel 4. In this embodiment, a rotation shaft 68 is provided on the end 67 of the pull lever 61, and a through hole (a through hole in this embodiment) or groove is correspondingly provided on one end of the diverting linkage 62, and a fastener such as a screw is used for positioning and affixation. The other end of the diverting linkage 62 is rotatably connected to one end of the locking hook liftable portion 63 in the same connection manner as the one end of the diverting linkage 62 is connected to the pull lever 61, not detailed again herein. A supporting rotation shaft point is provided between two ends of the diverting linkage 62 to fix this diverting linkage 62. Said supporting rotation shaft point can make the diverting linkage 62 rotate. In this embodiment, a rotation shaft hole 69 is provided on the diverting linkage 62 and a supporting rotation shaft 17 is provided at a corresponding position of the body of the base 10 to cooperate with the rotation shaft hole 69 so that the diverting linkage 62 can rotate along the support rotation shaft 17. To prevent the diverting linkage 62 from breaking away from the supporting rotation shaft 17 upon rotation, a fastener such as a screw is provided in the present invention to position and fix them.

In this embodiment, the locking hook liftable portion 63 is a locking hook liftable latch whose one end, as above discussed, is rotatably fixed on one end of the diverting linkage 62, and the other end of the locking hook liftable portion 63 is provided with a thrust surface 631 cooperating with the contact surface 59 on the liftable bracket 52. The thrust surface 631 has a ramp inclinded downwardly, the ramp of the locking hook liftable portion 63 extends out of the upper plane from the upper portion. Likewise, to prevent the locking hook liftable portion 63 from deviating from the movement path during forward and backward movement, a slide slot such as a opening is provided thereon to cooperate with the positioning post on the body of the base 10 so that the locking hook liftable portion 63 does not break away from the movement path during movement and meanwhile a screw is used for positioning and fixation.

Upon assembly, the fixed panel 64 at one end of the pull lever 61 is fixed to the operation key 41 and abuts against the button elastomer 43. In the present invention, a plurality of slide slots 66 are slideably fixed on the corresponding positioning posts 18 on the bottom of the body of the base 10 by fixing one end of the button elastomer 43, the fixed panel 64 and the operation key 41 together so that the slide slots 66 move along the positioning posts 18. One end of the diverting linkage 62 is rotatably fixed to another end 67 of the pull lever 61, the other end is rotatably fixed to one end of the locking hook liftable portion 63, the diverting linkage 62 is connected between the pull lever 61 and both ends of the locking hook liftable portion 63, the pull lever 61 and the locking hook liftable portion 63 are not on the same straight line but are angled to each other. In this embodiment, the diverting linkage 62 is angled to the pull lever 61 and the locking hook liftable portion 63 respectively at 55-60 degrees and 45-30 degrees. The diverting linkage 62 is rotatably fixed to the corresponding support shaft 17 on the base 10 via the rotation shaft hole 69 thereon so that the diverting linkage 62 can rotate around it as the supporting rotation shaft point. The locking hook liftable portion 63 is slideably fixed to the positioning post on the base 10 via the slide slot thereon.

Figure 10:
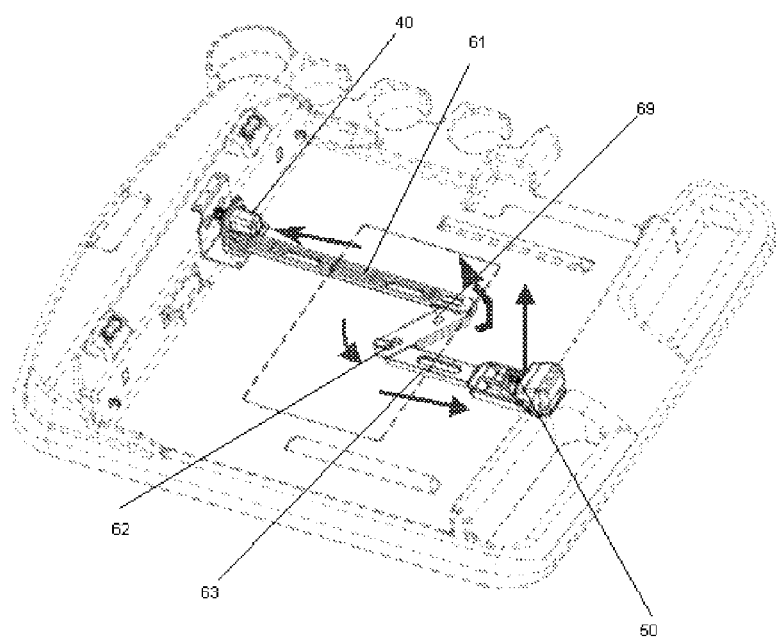

FIG. 4 and FIG. 10 are schematic views of the different states of the assembled transmission mechanism 60 being attached to the base 10 as seen from top and from the bottom. The operation mode of the fixing/releasing mechanism 20 of the present invention is illustrated in the following example in which the ultrasonic diagnosis apparatus is mounted to the base 10. Referring to FIG. 2, FIG. 4 and FIG. 10 again, when the ultrasonic diagnosis apparatus 30 is mounted to the platform 110 of the base 10, the rear end of the ultrasonic diagnosis apparatus 30 pushes and presses the operation key 41 of the press-fit button 40; when the ultrasonic diagnosis apparatus 30 is further pushed forward, the press-fit button 40, subjected to this push force, presses towards the fixed panel 64 of the pull lever 61 and the button elastomer 43 and urges the button elastomer 43 to compressedly move towards the button bracket 42 along the elastic support shaft 48, thereby also bringing the pull lever 61 to move backwardly. When the pull lever 61 moves backwardly, it pulls the end of the diverting linkage 62 connected thereto to move backwardly, the diverting linkage 62 rotates with the support rotation shaft 17 on the base 10 as the support point so that another end of the diverting linkage 62 connected to the locking hook liftable portion 63 moves forwardly so as to push the locking hook liftable portion 63 connected thereto to move forwardly, as shown in FIG. 10. When the thrust surface 631 of the locking hook liftable portion 63 moves forwardly, it moves in cooperation with the contact surface 59 of the snap catch mechanism 50 so that the horizontal movement of the locking hook liftable portion 63 is converted into a vertical protrudable and retractable movement of the snap catch mechanism 50 by means of the wedge structures of the ramps of the two, as shown in FIG. 7 and FIG. 8, that is to say, the liftable bracket 52, pushed by the locking hook liftable portion 63, moves upwardly along the positioning post 56 of the locking hook buffer 53 so as to bring the locking hook 51 to move upwardly to expose the body of the base 10 and be snap fitted in a hook slot on the bottom of the ultrasonic diagnosis apparatus 30 thereby fixing the ultrasonic diagnosis apparatus 30 to the base. When the bottom plane of the contact surface cooperates with the upper plane of the locking hook liftable portion, the positioning locking hook does not move upwardly any longer.

When the ultrasonic diagnosis apparatus 30 is removed, it is moved forwardly, the press-fit button 40, driven under the elastic return force of the button elastomer 43 therein, drives the operation key 41 and the fixed panel 64 of the pull lever 61 to move forwardly so as to bring the pull lever 61, the locking hook liftable portion 63 and the liftable bracket 52 of the snap catch mechanism 50 all to move in a direction opposite to the movement direction of the press-fit button 40 being applied a force so that the locking hook 51, after moving out of the hook slot on the bottom of the ultrasonic diagnosis apparatus 30, automatically and smoothly sinks into the locking hook receiving portion 139, thereby avoiding the possible damages caused by the locking hook 51 exposing on the base 10 when the ultrasonic diagnosis apparatus 30 breaks away from the base 10.

When the locking hook 51 moves out of the hook slot on the bottom of the ultrasonic diagnosis apparatus 30, the upward impact and collision generated between the locking hook 51, the press-fit button 40 and the ultrasonic diagnosis apparatus 30 is subsided by the ramp of the buffer top portion 55 of the locking hook buffer 53. The ramp of the buffer top portion 55 provides a slow and smooth movement for the moving out of the ultrasonic diagnosis apparatus 30 and effectively protects the ultrasonic diagnosis apparatus 30. At the same time, after the ultrasonic diagnosis apparatus 30 breaks away from the locking hook 51 and before the locking hook 51 completely sinks, it is raised to a certain height to prevent the locking hook 51 from colliding and damaging the medical apparatus during this process.

Figure 11:
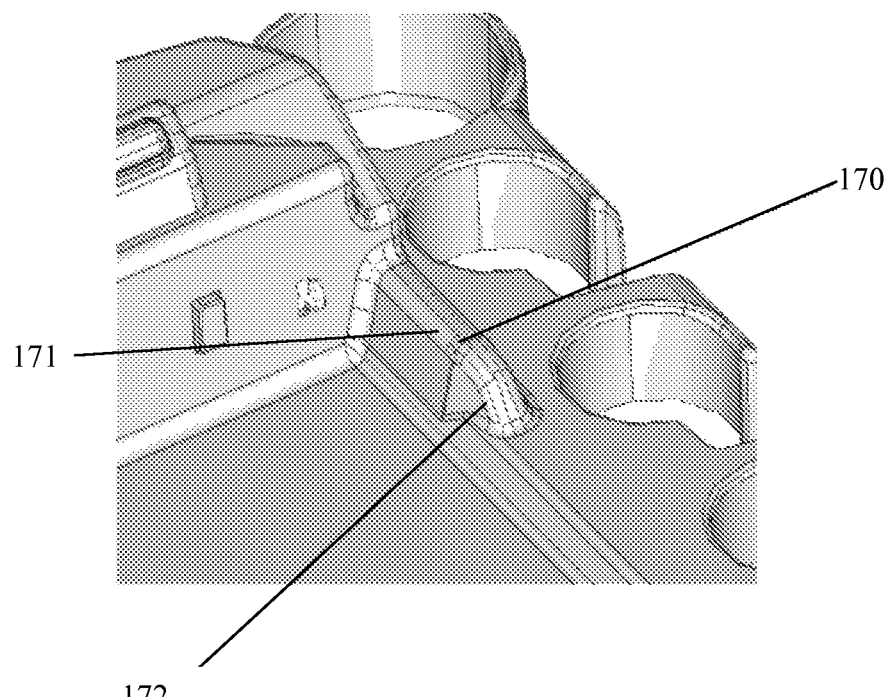
FIG. 11 is a partially enlarged view of a laterally mounted guide rail according to the present invention.
Figure 12:
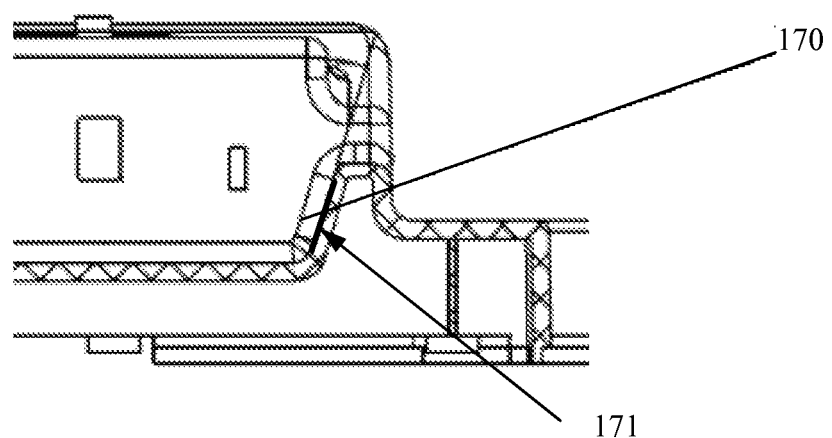
FIG. 12 is a view of the cross section of the first functional surface of the laterally mounted guide rail of FIG. 11.

As shown in FIG. 3 and FIG. 9, a laterally mounted guide rail 170 is provided on the left side and the right side of the base 10 adjacent to the rear side stand 130. Meanwhile, referring to FIG. 11 and FIG. 12, wherein FIG. 12 is a partial cross sectional view of FIG. 11 taken along the middle of the functional surface 171. Each laterally mounted guide rail 170 comprises a first functional surface 171 and a second functional surface 172 extending out along the first functional surface 171, the first functional surface 171 is a ramp extending upwardly and outwardly along the inside of the laterally mounted guide rail 170 from the platform 110 of the base 10 to allow the first functional surface 171 tangential to the end angle of the ultrasonic diagnosis apparatus 30 cooperating therewith to reduce friction between the two. The second functional surface 172 is also a ramp extending upwardly and outwardly along the inside of the laterally mounted guide rail 170 from the platform 110 of the base 10, the second functional surface 172 moves outwardly relative to the first functional surface 171 to form an angle between the first functional surface 171 and the second functional surface 172, the distance between the two rails is gradually increased to facilitate an operator removing and operating the ultrasonic diagnosis apparatus 30 to lessen impact force when the ultrasonic diagnosis apparatus 30 transmits from the first functional surface 171 to the second functional surface 172. The two laterally mounted guide rails 170 further enhance the precision of mounting the ultrasonic diagnosis apparatus 30 to the base 10 and reduces the operator's mounting and adjusting steps. Meanwhile, the two laterally mounted guide rails 170 buffer the impact to the ultrasonic diagnosis apparatus 30 caused by the press-fit button 40 or other locking hook for example a pair hooks 140a, 140b depicted hereunder and a connection plug 150 when the ultrasonic diagnosis apparatus 30 breaks away from the base, and meanwhile improve stability of the base 10.

Said base 10 further comprises a pair hooks 140a, 140b, a pair of top levers 180 and a connection plug 150, which project from the front side of the rear side stand 130. Hooks 140a, 140b and the connecting plug 150 respectively cooperate with a pair hook seats and a connection piece receiving member on one side of the rear surface of the ultrasonic diagnosis apparatus 30 to establish mechanical and electrical connection. When the ultrasonic diagnosis apparatus 30 moves out, the top lever 180 pushes forwardly the ultrasonic diagnosis apparatus 30 to make it away from the base.

Rails 160a, 160b extend from positions of the platform 110 of the base 10 adjacent to the left side and the right side respectively. This pair of rails 160a, 160b extend in a direction perpendicular to the front and rear stands 120, 130. The rails 160a, 160b respectively cooperate with a pair of sliders (not shown) on the bottom of the ultrasonic diagnosis apparatus 30 to facilitate mounting and positioning of the ultrasonic diagnosis apparatus 30.

The press-fit button 40, the snap catch mechanism 50 and the transmission mechanism 60 in the fixing/releasing mechanism 20 can also be of the following configuration: the pull lever 61, the diverting linkage 62, and the locking hook liftable portion 63 in the transmission mechanism 60 form an integral straight-rod-type locking hook liftable portion, which front end is in a shape of wedge, has a ramp inclined upwardly, wherein the ramp cooperates with the contact surface 59 of the liftable bracket 52 of the snap catch mechanism 50. Another end is the fixed panel 64 located between the press-fit button 40 above the body of the base 10 and the transmission mechanism 60 below the body of the base 10 and connected to the operation key 41 of the press-fit button 40 and the fixed panel 64 of the transmission mechanism 60 via the restorable button elastomer. When the press-fit button 40 is pushed and pressed, it compresses the elastomer and urges the elastomer to push and press towards the transmission mechanism 60 to push the transmission mechanism 60 to move horizontally forwardly. The wedge-shaped structure of the transmission mechanism 60 converts the horizontal movement of the transmission mechanism 60 into an up-and-down protrudable and retractable movement of the snap-catch mechanism 50, thereby achieving the object of raising the locking hook 51 to expose out of the body of the base 10 to lock the ultrasonic diagnosis apparatus 30. When the thrust force of the press-fit button 40 is erased or lessened and the locking hook 51 breaks away from the ultrasonic diagnosis apparatus 30, the elastomer connected between the press-fit button 40 and the transmission mechanism 60, due to an elastic return force, pushes the press-fit button 40 to return to the original position and bring the transmission mechanism 60 to move backwardly. Meanwhile, due to the elastic return force of the snap catch elastomer 54 in the snap catch mechanism 50, the liftable bracket 52 moves downwardly to return to the original position and pushes the transmission mechanism 60 to move backwardly, which facilitates the return of the press-fit button 40 and return of the locking hook 51 to the origianl position.

In the present invention, so long as one of the contact surfaces of the transmission mechanism 60 and the snap catch mechanism 50 is wedge-shaped, the horizontal movement of the transmission mechanism 60 can be converted into the up-and-down movement of the snap catch mechanism 50.

In the present invention, the transmission diverting means can be a gear mechanism which is connected between the pull lever and the locking hook liftable portion, the gear is brought into rotation by means of forward or backward movement of the pull lever so that the rotation of the gear brings backward or forward movement of the locking hook liftable portion.

In the present invention, the fixing/releasing mechanism can be disposed on an apparatus such as the ultrasonic diagnosis apparatus 30.

What is claimed is:

1. A fixing/releasing mechanism configured to connect a first unit and a second unit and mounted on the first unit, said mechanism comprising:

a press-fit button configured to move when under a pressure, said press-fit button configured to move in a direction of the pressure and to automatically return to the original position when the applied pressure disappears;

a snap catch mechanism comprising a lock hook configured to couple the first unit to the second unit and to release the second unit from the first unit, said snap catch mechanism further comprising a lock hook buffer, wherein, upon mounting, said lock hook buffer is fixed on the first unit, and wherein said lock hook buffer comprises an inclined top portion that is exposed on a front surface of the first unit to buffer impact generated when said lock hook releases the second unit; and a transmission mechanism connected to said press-fit button and configured to transmit the pressure applied to said press-fit button to said snap catch mechanism such that said lock hook generates protrudable and retractable movement in order to fix the first unit to the second unit or to release the second unit from the first unit.

2. The fixing/releasing mechanism according to claim 1, wherein:

said snap catch mechanism further comprises a liftable bracket comprising a lock hook base and said lock hook, said lock hook extending upwardly from said lock hook base;

a contact surface disposed on said lock hook base in a direction opposite to the extension direction of said lock hook; and said transmission mechanism comprising a lock hook liftable portion, said lock hook liftable portion comprising a latch comprising a push surface oriented such that said push surface contacts said contact surface and is moveable forward and backward relative to said contact surface in order to bring the protrudable and retractable movement of said lock hook base and said lock hook.

3. The fixing/releasing mechanism according to claim 2, wherein:

each of said push surface front end and said contact surface front end comprises a downwardly inclined ramp, said contact surface further comprises a bottom plane extending out from the bottom of said contact surface front end ramp; and said push surface further comprises an upper plane extending from an upper portion of the ramp.

4. The fixing/releasing mechanism according to claim 3, wherein:

said snap catch mechanism further comprises a lock hook elastomer such that said locking hook elastomer is disposed between a lower surface of the top portion of said locking hook buffer and said locking hook base such that said locking hook elastomer abuts against said lock hook base surface on one side of the extension direction of said locking hook;

a plurality of positioning posts extend out from a lower surface of the top portion of said lock hook buffer;

said locking hook base comprises a plurality of through holes matching said plurality of positioning posts; and said lock hook elastomer comprises a plurality of springs sleeved onto the positioning posts.

5. The fixing/releasing mechanism according to claim 2, wherein:

said press-fit button comprises an operation key and a button elastomer;

said transmission mechanism comprises a fixed panel located at a second end opposite to a first end of said push surface; and said button elastomer is configured to move said fixed panel according to a push force transmitted by the operation key and to push said push surface along the contact surface.

6. The fixing/releasing mechanism according to claim 5, wherein said button elastomer comprises a spring having a first end and an opposite second end respectively connected to said operation key and said fixed panel.

7. The fixing/releasing mechanism according to claim 5, wherein:

said press-fit button further comprises a button bracket that is, upon mounting, fixed to the first unit;

said operation key is fixed to said fixed panel and the button elastomer abuts against between said fixed panel of the transmission mechanism and the button bracket; and said button bracket comprises a supporting planar body supporting and abutting against said button elastomer, and an upper fixed planar body and a lower fixed planar body extending along both ends of said supporting planar body towards each other, said supporting planar body comprising an elastic support shaft oriented to support said button elastomer and position movement of said button elastomer and said operation key, said upper fixed planar body and said lower fixed planar body are fixed to the first unit upon mounting.

8. The fixing/releasing according to claim 7, wherein said transmission mechanism further comprises a pull lever and a diverting transmission means, a first end of said pull lever comprises said fixed panel fixedly connected to said operation key, an opposite second end is connected to a first end of said diverting transmission means, an opposite second end of said diverting transmission means is connected to said second end of said lock hook liftable portion opposite to a first end of said push surface, and wherein said diverting transmission means is connected between said pull lever and said first and second ends of said lock hook liftable portion in order to transmit the movement of said pull lever to said lock hook liftable portion and to convert forward or backward movement of said pull lever into backward or forward movement of said lock hook liftable portion.

9. The fixing/releasing mechanism according to claim 8, wherein said diverting transmission means comprises a diverting linkage rotatably connected between said pull lever and said first and second ends of said lock hook liftable portion to enable said pull lever and said lock hook liftable portion not to be on the same straight line such that upon mounting, at any position between said first and second ends of said diverting linkage is provided a supporting rotation shaft point by virtue of which said diverting linkage is rotatably fixed to the first unit, and wherein said diverting transmission means comprises a gear.

10. The fixing/releasing mechanism according to claim 8, wherein each of said pull lever and said lock hook liftable portion comprise a slide slot so as to be slidingly fixed to the first unit upon mounting.

11. A base for placement of a medical apparatus, comprising:

a base body comprising a platform configured to carry the medical apparatus; and a fixing/releasing mechanism configured to fix and release the medical apparatus, said fixing/releasing mechanism comprising a lock hook for fixing/releasing the medical apparatus, said fixing/releasing mechanism further comprises:

a press-fit button comprising an operation key exposed above said base body, said operation key is protrudably and retractably received in a key through hole in said base body, said operation key configured to move in a direction of a force when being subjected to a pressure to be received in said key through hole such that when the applied force disappears, said operation key automatically returns to the original position and protrudes out of said key through hole;

a snap catch mechanism comprising said lock hook protrudably and retractably received in a lock hook receiving portion in said base body, said snap catch mechanism further comprising a lock hook buffer, wherein said lock hook buffer is fixed on a snap catch mechanism seat of said base body and comprises an inclined top portion that is exposed outside of said base body to buffer impact generated when said lock hook releases the medical apparatus; and a transmission mechanism connected to said press-fit button and configured to transmit the pressure applied to said press-fit button to said snap catch mechanism such that said lock hook generates a protrudable and retractable movement and protrudes out of said lock hook receiving portion to lock the medical apparatus or retract in said lock hook receiving portion and release the medical apparatus.

12. The base for placement of a medical apparatus according to claim 11, wherein:
said snap catch mechanism further comprises a liftable bracket comprising a lock hook base and said lock hook, said lock hook extending upwardly from said lock hook base, a contact surface being disposed on said lock hook base in a direction opposite to the extension direction of said lock hook;
said transmission mechanism comprises a lock hook liftable portion comprising a latch and a push surface, said push surface being able to contact said contact surface and moveable forward and backward relative to said contact surface so as to bring the protrudable and retractable movement of said lock hook base and said lock hook.

13. The base for placement of a medical apparatus according to claim 12, wherein:
each of said push surface front end and said contact surface front end comprise a downwardly inclined ramp, said contact surface further comprising a bottom plane extending out from a bottom of said contact surface front end ramp, said push surface comprises an upper plane extending from an upper portion of said push surface front end ramp.

14. The base for placement of a medical apparatus according to claim 13, wherein: said snap catch mechanism further comprises a lock hook elastomer, said locking hook elastomer is disposed between a lower surface of a top portion of said locking hook buffer and said lock hook base such that said locking hook elastomer abuts against said lock hook base surface on a first side of the extension direction of said lock hook.

15. The base for placement of a medical apparatus according to claim 14, further comprising a plurality of positioning posts that extend out from a lower surface of said top portion of said lock hook buffer, wherein said locking hook base comprises a plurality of through holes matching said plurality of positioning posts, said lock hook elastomer comprises a plurality of springs sleeved onto said positioning posts, and said lock hook buffer is fixed to said snap catch mechanism seat via said plurality of positioning posts in cooperation with screws.

16. The base for placement of a medical apparatus according to claim 12, wherein:
said press-fit button further comprises a button elastomer; and
said transmission mechanism comprises a fixed panel located at a second end opposite to a first end of said push surface of the lock hook liftable portion, said button elastomer configured to move said fixed panel according to the push force transmitted by said operation key and to push said push surface of said transmission mechanism to move along said contact surface of said snap catch mechanism.

17. The base for placement of a medical apparatus according to claim 16, wherein:
said button elastomer comprises a spring having a first end and an opposite second end respectively connected to said operation key of said press-fit button and said fixed panel of said transmission mechanism;
said press-fit button further comprises a button bracket fixed to said base body;
said operation key is fixed to said fixed panel and said button elastomer abuts against between said fixed panel and said button bracket;
said button bracket comprises a supporting planar body supporting and abutting against said button elastomer, and an upper fixed planar body and a lower fixed planar body that extend along both ends of said supporting planar body towards each other; other, wherein said supporting planar body comprises an elastic support shaft to support said button elastomer and position movement of said button elastomer, said fixed panel and said operation key, said upper fixed planar body and said lower fixed planar body are fixed to said base body.

18. The base for placement of a medical apparatus according to claim 17, wherein said transmission mechanism further comprises a pull lever and a diverting transmission means, a first end of said pull lever comprises said fixed panel fixedly connected to said operation key, an opposite second end is connected to a first end of said diverting transmission means, an opposite second end of said diverting transmission means is connected to said second end of said lock hook liftable portion opposite to a first end of said push surface, and wherein said diverting transmission means is connected between said pull lever and said first and second ends of said lock hook liftable portion in order to transmit the movement of said pull lever to said lock hook liftable portion and to convert forward or backward movement of said pull lever into backward or forward movement of said lock hook liftable portion.

19. The base for placement of a medical apparatus according to claim 18, wherein said diverting transmission means comprises a diverting linkage rotatably connected between said pull lever and said first and second ends of said lock hook liftable portion to enable said pull lever and said lock hook liftable portion not to be on the same straight line such that upon mounting, at any position between said first and second ends of said diverting linkage is provided a supporting rotation shaft point by virtue of which said diverting linkage is rotatably fixed to the first unit, and wherein said diverting transmission means comprises a gear.

20. The base for placement of a medical apparatus according to claim 11, wherein at said first and second ends of said platform two side stands extend upwardly from said base body, said two side stands being a front and a rear side stands said lock hook receiving portion is provided on the platform adjacent to the front side stand, said transmission mechanism is provided on said lower portion of said base body; on said platform of said base body a side mounting guide rail extends from at least one of left and right sides adjacent to said rear side stand, said side mounting guide rail comprises a first functional surface and a second functional surface extending out along said first functional surface, said first and second functional surfaces comprise ramps extending upwardly and outwardly along an inside of said side mounting guide rail from said platform such that said first functional surface is tangential to an end angle of the medical apparatus cooperating therewith; said second functional surface moves outwardly relative to said first functional surface and an angle is formed between said first functional surface and said second functional surface.

* * * * *